(12) United States Patent
Blau et al.

(10) Patent No.: US 7,094,501 B2
(45) Date of Patent: Aug. 22, 2006

(54) GRAFT OLIGOMERIC ELECTROLYTES

(75) Inventors: Hanne Anna Katharina Blau, Wilmington, DE (US); Pui-Yan Lin, Hockessin, DE (US); José Manuel Rodriguez-Parada, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 436 days.

(21) Appl. No.: 09/962,173

(22) Filed: Sep. 25, 2001

(65) Prior Publication Data

US 2003/0059683 A1 Mar. 27, 2003

(51) Int. Cl.
*H01M 10/40* (2006.01)

(52) U.S. Cl. .............. 429/316; 429/304; 429/306; 429/317; 521/25; 568/24; 568/35

(58) Field of Classification Search ........... 429/188, 429/304, 306, 314, 305, 316, 317; 521/25; 427/58, 220, 336; 568/24, 35
See application file for complete search history.

(56) References Cited

U.S. PATENT DOCUMENTS

| | | | |
|---|---|---|---|
| 5,032,306 A | | 7/1991 | Crips |
| 5,552,510 A | | 9/1996 | Sanchez et al. |
| 5,696,224 A | | 12/1997 | Delabouglise et al. |
| 6,033,804 A | * | 3/2000 | Doyle et al. ............ 429/212 |
| 6,063,522 A | | 5/2000 | Hamrock et al. |

FOREIGN PATENT DOCUMENTS

| WO | WO/ 99/05189 | 2/1999 |
|---|---|---|
| WO | WO 00/22012 | 4/2000 |

OTHER PUBLICATIONS

Ranganathan, et al., "Peroxide–initiated Grafting of Maleic Anhydride onto Linear and Branched Hydrocarbons", Journal of Polymer Science: Part A: Polymer Chemistry, (1999), pp. 3817–3825, vol. 37, Canada.
Forsyth, et al., "Peroxide–initiated Vinylsilane Grafting: Structural Studies on a Hydrocarbon Substrate", Journal of Polymer Science: Part A: A Polymer Chemisty, (1997), pp. 3517–3525, vol. 35, Canada.
D.C. Clark, et al., "Dual Monomer Grafting os Styrene and Maleic Anhydride onto Model Hydrocarbon Substrates", Journal of Polymer Science: Part A: Polymer Chemistry, (1999), pp. 2456–2468, vol. 38, Canada.
Ranganathan, et al., "Peroxide–Initiated Grafting of Maleic Anhydride onto Linear and Branched Hydrocarbons", Journal of Polymer Science: Part A: Polymer Chemistry, (1999), pp. 3817–3825, vol. 37, Canada.
Forsyth, et al., "Peroxide–Initiated Vinylsilane Grafting: Structural Studies on a Hydrocarbon Substrate", Journal of Polymer Science: Part A: Polymer Chemistry, (1997), pp. 3517–3525, vol. 35, Canada.
D.C. Clark, et al., "Dual Monomer Grafting os Styrene and Maleic Anhydride onto Model Hydrocarbon Substrates", Journal of Polymer Science: Part A: Polymer Chemistry, (1999), pp. 2456–2468, vol. 38, Canada.
PCT/US 02/30432 International Search Report Dated Feb. 1, 2005.

* cited by examiner

*Primary Examiner*—Michael Barr
*Assistant Examiner*—Monique Wills

(57) ABSTRACT

Disclosed are compositions prepared by free-radical-driven grafting onto hydrocarbons or hydrocarbon ethers of olefinically unsaturated fluorocarbons containing sulfonyl fluoride, fluorosulfonate, fluorosulfonimide, or fluorosulfonyl methide groups, wherein the grafting step is followed by a hydrolysis step in the case of sulfonyl fluoride.

29 Claims, No Drawings

GRAFT OLIGOMERIC ELECTROLYTES

FIELD OF THE INVENTION

The present invention deals with a new class of compositions suitable for use as electrolytes in electrochemical cells, with particular utility in lithium batteries. The compositions are prepared by free-radical-driven grafting onto hydrocarbons or hydrocarbon ethers of olefinically unsaturated fluorocarbons containing sulfonyl fluoride, fluorosulfonate, fluorosulfonimide, or fluorosulfonyl methide groups, wherein the grafting step is followed by a hydrolysis step in the case of sulfonyl fluoride.

TECHNICAL BACKGROUND OF THE INVENTION

In electrochemical cells such as lithium batteries, the charge carrying entity of interest is the metallic cation, such as lithium, while the anion is not involved with the current-producing electrochemical processes at either electrode. Any transport of charge by the counterion, (the anion in the case of a lithium battery) is undesirable because it leads to concentration polarization of the electrolyte in the cell reducing the charge/discharge rate capability of the cell. In the ideal lithium cell with high power density, lithium ions would be of high concentration and exhibit high mobility, resulting in high conductivity while the counterion would exhibit virtually no mobility, thereby resulting in a high lithium transference number where lithium transference number refers to the number of moles of Li+ transferred for the passage of 1 faraday of electricity.

Rechargeable lithium-ion cells typically use liquid or gelled polymer electrolytes consisting of inorganic lithium salts, such as $LiPF_6$, in an organic solvent. Such electrolytes exhibit high conductivity but the anions have high mobility, often exhibiting a Li transference number of around 0.3.

Similar trade-offs exist when solutions of organic salts having larger counterions, such as perfluoroalkylsulfonates, sulfonimides, and sulfonyl methides such as are disclosed in Waddell et al, U.S. Pat. No. 5,514,493. With most of these salts the transference number of Li is lower than 0.5.

Another approach is to employ solid polymer electrolytes, where the lithium ion is a labile ion attached to a polymeric chain which acts as the anion. See, for example, Narang et al, U.S. Pat. No. 5,633,098 and DesMarteau, U.S. Pat. No. 5,463,005. These materials typically provide very high lithium transference numbers and the cells would exhibit virtually no concentration polarization under load. However, low inherent ionic conductivities, insufficient electrochemical stability, and difficulty in processing limit their usefulness.

Hamrock et al, U.S. Pat. No. 6,063,522 discloses solutions of hybrid fluorocarbon and hydrocarbon imide and methide salts. Included are polymers formed by free-radical polymerization of monomers having hydrocarbon backbones and pendant groups of fluorinated sulfonyl imides linked thereto by carbonyl or phenylsulfonyl connecting groups. Also included are copolymers formed by copolymerizing said monomers with low polarity olefinic comonomers.

Grafting of various monomers onto hydrocarbons by free radical methods is disclosed in *J. Polym. Sci., Part A: Polym. Chem.* (1997), 35, 3517, *Polym. Sci., Part A: Polym. Chem.* (1999), 37, 3817, and *Polym. Sci., Part A: Polym. Chem.* (2000), 38, 2456. In these studies hydrocarbons were used as models for polyolefins. No mention of fluorocarbon monomers is made.

Cripps, U.S. Pat. No. 5,032,306 discloses free radical grafting of perfluoroalkenes and perfluorovinyl ethers onto hydrocarbons having at least four carbon atoms. Examples include hexafluoropropylene and perfluoropropyl vinyl ether monomers. No mention is made of monomers containing perfluoroalkylsulfonate, sulfonimide, or sulfonyl methide groups.

SUMMARY OF THE INVENTION

The present invention provides for a composition comprising a saturated acyclic aliphatic hydrocarbon radical, said hydrocarbon radical having disposed thereupon at least one pendant group represented by the formula

wherein said hydrocarbon radical is optionally substituted with one or more ether oxygens;

wherein $R_f$ is represented by the formula

where a=0 or 1, b=0 or 1, c=0,1 or 2; —Q— is represented by the formula

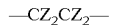

where Z is H, F, alkyl or fluoroalkyl with the proviso that not more than one Z may be alkyl or fluoroalkyl; $R_f'$ is F or a perfluoroalkyl radical having 1–10 carbons optionally substituted by one or more ether oxygens; X is F or —Y(M)$(SO_2R_f'')_p$ wherein p=0–2, with the proviso that Y is O when p=0, Y is N when p=1, and Y is C when p=2, M is an alkali metal cation or H+, and $R_f''$ is a perfluoroalkyl radical having 1–10 carbons optionally substituted with one or more ether oxygens, or $R_f''$ is CN when p=2.

The present invention further provides for a process for forming a composition, the process comprising contacting in the presence of a free radical initiator a saturated acyclic aliphatic hydrocarbon optionally substituted with one or more ether oxygens with an olefinically unsaturated fluorocarbon and, heating in order to decompose the initiator and form free radicals; said olefinically unsaturated fluorocarbon being represented by the formula

where Z is H, F, alkyl or fluoroalkyl with the proviso that not more than one Z may be alkyl or fluoroalkyl; $R_f'$ is F or a perfluoroalkyl radical having 1–10 carbons optionally substituted by one or more ether oxygens; and X is F or —Y(M)$(SO2R_f'')_p$ wherein p=0–2, with the proviso that Y is O when p=0, Y is N when p=1, and Y is C when p=2, M is an alkali metal cation or H+, and $R_f''$ is a perfluoroalkyl radical having 1–10 carbons optionally substituted with one or more ether oxygens.

Further provided is an electrolyte composition comprising the composition of the invention and a liquid, a polymer or a mixture thereof combined therewith.

Further provided is an electrochemical cell comprising a positive electrode, a negative electrode, a separator, and the electrolyte composition of the invention said anode, cathode, separator, and electrolyte composition being in ionically conductive contact with one another.

DETAILED DESCRIPTION OF THE INVENTION

This invention provides oligomeric compositions prepared by contacting olefinically unsaturated fluorocarbons containing a fluorosulfonyl fluoride, fluorosulfonate, fluorosulfonyl imide or fluorosulfonyl methide group with a hydrocarbon or a hydrocarbon ether, including polyethers, in the presence of free radical initiators to form a grafted composition. The composition so produced, or an ionic derivative thereof in the case of the sulfonyl fluoride, is useful as an electrolyte in electrochemical cells, most particularly, lithium batteries. The oligomeric lithium ion electrolyte compositions of the present invention exhibit an excellent balance between ionic conductivity and lithium transference number.

Particularly suitable for the process of the present invention are saturated acyclic aliphatic hydrocarbons having 6–30 carbon atoms in the aliphatic chain optionally substituted by one or more ether oxygens. In order for the grafting reaction to proceed, the hydrocarbon suitable for the practice of the present invention must have hydrogens that can be abstracted by the free radical initiator. Tertiary carbons will exhibit the highest propensity for the grafting reaction of the invention while primary carbons, the lowest. Only a small amount of product has a graft formed at a terminal $CH_3$ groups. Most linear and branched saturated acyclic aliphatic hydrocarbons are suitable. Pure compounds, that is single homologues, as well as mixtures thereof such as mineral oils and commercial waxes can be used in the process of the invention. Single homologues are preferred. Acyclic saturated hydrocarbons containing heteroatoms in the aliphatic chain such as those obtained from oligomerization of ethylene oxide, propylene oxide, and their mixtures are also suitable. Unsaturated hydrocarbons may lead to cross-linked structures which defeats the purpose of the invention. Most preferred for the practice of the invention are dodecane and poly(ethylene oxide) oligomers ranging in molecular weight from ca. 100 to ca. 2000 Daltons. Free-radical initiators suitable for the process of the invention are well-known in the art for use in initiating olefin polymerizations. These include inorganic and organic peroxides and azo compounds. Organic peroxides are the preferred initiators with tert-butyl peroxide and dicumyl peroxide most preferred. The amount of initiator used is between 1 and 20 weight % of the hydrocarbon polymer preferably from 5 to 10 weight %. In most cases it is preferred to use excess hydrocarbon since it is the cheaper ingredient and the product is usually not soluble in it. We base the amount of initiator on the amount of hydrocarbon because the main reaction is hydrogen abstraction from the hydrocarbon by the radicals obtained from the decomposition of initiator.

Hydrocarbons suitable for the process of the invention can be used neat or in solution. Suitable solvents include aromatic hydrocarbons such as chlorobenzene and dichlorobenzene, halogenated hydrocarbons, and polar aprotic solvents such as dimethyl acetamide and dimethyl formamide. Chlorobenzene is the most preferred. In general the ingredients suitable for the process of the invention exhibit sufficient mutual solubility that an additional solvent is not necessary, and therefore use of an additional solvent is not preferred. If one reactant is of relatively high MW, for example a hydrocarbon wax, a solvent may be preferred over preheating the ingredients.

Suitable fluorocarbons are represented by the formula

$CZ_2=CZ-O_a-(CF_2CFR_f'-O_b)_c CF_2CF_2-SO_2X$ where Z is H, F, alkyl or fluoroalkyl with the proviso that not more than one Z may be alkyl or fluoroalkyl; $R_f'$ is F or a perfluoroalkyl radical having 1–10 carbons; and X is F or $-Y(M)(SO2R_f'')_p$ wherein p=0–2, with the proviso that Y is O when p=0, Y is N when p=1, and Y is C when p=2, M is an alkali metal cation or H+, and $R_f''$ is a perfluoroalkyl radical having 1–10 carbons optionally substituted with one or more ether oxygens.

Preferably, Z is F or H, a=0 or 1, b=1, c=0 or 1, and X is F, with the proviso that when Z is H, a=0. Most preferably, Z is F, a=1, b=1, and c=1, and X is F.

In one embodiment of the process of the invention the grafting reaction is carried out by dispersing the fluorocarbon and free-radical initiator in a liquid hydrocarbon suitable for the practice of the invention. The mixture is stirred under an inert atmosphere. Reaction temperatures can range from room temperature to about 160° C. depending on the solubility of the fluorocarbon and the decomposition temperature of the initiator. The most preferred range is between 80 and 130° C. Nitrogen and argon provide suitably inert atmospheres. The grafting reaction can be stopped by exhaustion of initiator or by lowering the temperature to reduce the decomposition rate of the initiator. Isolation of the product is conveniently carried out by evaporation of unreacted components. In the case of dodecane and lower hydrocarbons the grafted product is not soluble in the hydrocarbon, thus forming two liquid layers which can be easily separated. Another method for separating the product is precipitation into a non-solvent such as pentane or hexane.

Fluorocarbons in the form of an imide, methide, or sulfonate are in general not soluble in hydrocarbons but are soluble in polyether oligomers such as poly(ethylene oxide), which is then preferred.

There is no specific order of mixing of ingredients if it is done at low temperature before reaction starts. If the reactants are preheated, then it would be wise to add the initiator last and slowly.

If the fluorocarbon contains a sulfonyl fluoride group, it may be converted to an acid, salt, imide, or methide according to methods known in the art. A preferred fluorocarbon is perfluoro(3,6-dioxa-4-methyl-7-octenesulfonyl fluoride) (PSEPVE) which can be made by pyrolysis of the corresponding acid fluoride as described in detail by Connolly et al. in U.S. Pat. No. 3,282,875. The terms PSEPVE-imide, PSEPVE-methide, or PSEPVE-sulfonate shall be taken to mean the imide, methide, and sulfonate derivatives respectively converted from the sulfonyl fluoride-containing PSEPVE according to the methods outlined herein. While PSEPVE is not ionic in nature, PSEPVE-imide, PSEPVE-methide, and PSEPVE-sulfonate are all ionic in nature, requiring the presence of an alkali metal or alkaline earth metal cation, preferably lithium, and are thus referred to as salts.

Conversion of sulfonyl fluorides to imides can be accomplished by reacting them with perfluoroalkylsulfonamides. The reaction is typically run in polar aprotic solvents such as, but not limited to, acetonitrile, tetrahydrofuran, and dimethylsulfoxide. at temperatures between 0 and 100° C. A molar excess of a tertiary amine, such as triethylamine or pyridine, is preferably used to drive the reaction and neutralize the HF formed. The resulting ammonium imide salt is then treated with the appropriate base to effect an exchange of the ammonium ion for the desired cation. Detailed procedures for the preparation of this type of salt are given in DesMarteau et al. *Inorg. Chem.*, 1990, 29, 2982–2985, and in Waddell et al, op.cit., and Hamrock et al, WO 99/49529. Alternatively, the sulfonyl fluorides can be reacted with dimetal sulfonylamide salts such as $CF_3SO_2NNa_2$ to obtain the corresponding imides. This method is particularly useful for sensitive substrates and yields high conversions. It is described in detail in Blau, WO 01/40174.

Methide salts can be made by reacting the sulfonyl fluoride with appropriate disubstituted methanes. In one embodiment, a disubstituted methane is reacted with two equivalents of a strong base and the resulting anion is then reacted with the sulfonyl fluoride to form a methide anion. Again polar aprotic solvents and temperatures between 0 and 100° C. are often used. Processes useful for the synthesis of a variety of methide salts are found in patents U.S. Pat. No. 5,514,493 and Hamrock et al, op.cit. Dicyanomethide salts can be easily prepared by reacting the sulfonyl fluorides with commercially available malononitrile and lithium hydride at room temperature in tetrahydrofuran. Specific procedures to prepare dicyanomethide salts are given in Feiring et al, WO 99/45048.

The oligomeric salts of the present invention can be easily purified by dialysis of their aqueous solutions. Proper choice of membrane pore size eliminates all the low molecular weight excess reactants and impurities.

When the process of the invention is carried out according the methods set forth herein, the result is a graft oligomer composition comprising a saturated acyclic aliphatic hydrocarbon radical optionally substituted with one or more ether oxygens, said hydrocarbon radical optionally substituted with one or more ether oxygens having disposed thereupon at least one pendant group represented by the formula

wherein $R_f$ is represented by the formula

where a=0 or 1, b=0 or 1, c=0,1 or 2; —Q— is represented by the formula

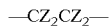

where Z is H, F, alkyl or fluoroalkyl with the proviso that not more than one Z may be alkyl or fluoroalkyl; $R_f'$ is F or a perfluoroalkyl radical having 1–10 carbons optionally substituted by one or more ether oxygens; X is F or —Y(M)($SO_2R_f''$)$_p$ wherein p=0–2, with the proviso that Y is O when p=0, Y is N when p=1, and Y is C when p=2, M is an alkali metal cation or $H^+$, and $R_f''$ is a perfluoroalkyl radical having 1–10 carbons optionally substituted with one or more ether oxygens, or $R_f''$ is CN when p=2.

In one embodiment of the graft oligomer of the invention the hydrocarbon radical is a radical having 6–30 carbons disposed in a linear chain optionally substituted by one or more ether oxygens, or is a radical formed from a polyether of molecular weight between 100 and 2000 daltons. Preferred are a hydrocarbon radical derived from dodecane and a polyethylene oxide having a molecular weight between 100 and 2000 Daltons.

The graft oligomers obtained by this process contain from 10 to 90 weight percent of pendant fluorocarbon side chains. The degree of grafting depends on the temperature and on the concentration of substrate, fluoromonomer, and initiator. The grafted materials obtained by this process are not crosslinked and are therefore soluble in most common organic solvents. Depending on the substrate and the degree of grafting the materials range from viscous liquids to soft semicrystalline compounds at room temperature. One of skill in the art will appreciate that side reactions such as chain scission and radical recombination will occur while the grafting reaction takes place. Consequently the final product will be a mixture of grafted hydrocarbons (or polyethers) differing in chain length and branching frequency.

The ionic graft oligomers of the present invention are useful as electrolytes in electrochemical cells when dissolved in a suitable solvent. In one embodiment, the graft ionic oligomer of the present invention forms a liquid electrolyte solution when combined with a liquid electrolyte solvent such as water, alcohol, a mixture thereof, or one or more aprotic solvents. Particularly preferred are organic carbonate solvents which include acyclic and cyclic organic carbonates, primarily dimethyl carbonate (DMC), diethyl carbonate (DEC), ethyl methyl carbonate (EMC), propylene carbonate (PC), and ethylene carbonate (EC), most preferably EC or PC, and monoesters such as methyl acetate (MA), ethyl acetate (EA), methyl formate (MF), methyl propionate (MP), ethyl propionate (EP), and gamma-butyrolactone (GBL), as well as diesters, preferably dimethyl succinate as well as others as described in Doyle et al, WO 0103230. Most often, these liquid electrolyte solvents are used in combinations such as a cyclic organic carbonate, preferably EC or PC, at a concentration in the range of 0.1 to 3 molar, preferably 0.5 to 1.5 molar based upon the concentration of the mobile cation, and an acyclic carbonate, usually DMC, DEC, or EMC, as disclosed in Okuno et al, U.S. Pat. No. 5,525,443. These combinations have been found in practice to achieve an excellent combination of desirable properties such as high ionic conductivity over a wide temperature range and relatively low volatility while achieving excellent lifetime and performance in lithium-ion batteries.

In another embodiment, the liquid electrolyte solution of the invention is incorporated into an electrochemical cell, preferably a lithium or lithium ion cell. The lithium-ion cell of the present invention comprises a positive electrode, a negative electrode, and a separator, at least one of which, preferably all of which, will be in ionically conductive contact with the electrolyte solution of the invention. The lithium-ion cell will also contain current collectors typically composed of either foils or meshes or metallized plastics where the metal is composed of aluminum (for the cathode) and copper (for the anode). One of skill in the art will recognize that under normal operating circumstances, all of the components of the cell will be in said contact, since it is by virtue of said ionically conductive contact among the components of the cell that the cell operates.

In an alternative embodiment of the electrolyte composition of the invention, a solid polymer electrolyte is formed by combining the ionic graft oligomer of the invention with a solid polymer having high donor number wherein the solid polymer serves to replace the liquid electrolyte solvent above. Particularly preferred are polymers with strong electron donor characteristics which include polymers with ethylene oxide or propylene oxide linkages such as poly (ethylene oxide), and comb-shaped polyethers like those described by Ikeda et al., *Electrochimica Acta* 45 1167–1174 (2000), including poly[bis-(methoxyexothyethoxide) phosphazene]. The solid polymer electrolyte of the invention may be formed by any convenient method. For example, the graft oligomer, generally in ionic form, may be dissolved in a solvent which also swells the solid polymer, so that when the solution of graft oligomer is contacted with the solid polymer, the graft oligomer will be imbibed within the solid polymer, following which the solvent can be driven off. In another embodiment, a monomer having high donor number may be combined with the graft oligomer, generally in ionic form, followed by in-situ polymerization of the monomer to form the solid polymer electrolyte of the invention. In one embodiment, the solid polymer is a polyethylene oxide. In other embodiments, the polymers are poly [(poly (ethylene glycol) methyl ether methacrylate], or polyvinyl ether. In another embodiment, the solid polymer is poly [(poly (ethylene glycol) methyl ether acrylate]. In this embodiment, the monomeric poly(ethylene glycol) methyl ether acrylate is readily mixed with the graft oligomer of the invention and then the acrylate monomer is polymerized in situ by for example a photoinitiated free radical polymerization. In one particular embodiment, the graft oligomer therein employed is an imide or methide grafted polyethylene oxide wherein the polyethylene oxide moiety has a molecular weight of ca. 250 Daltons.

In a further embodiment, the liquid electrolyte solution of the invention is combined with at least one component of a lithium-ion battery, the components thereof being a positive electrode, a negative electrode, and a separator in accord with the teachings of the art. In the case of the positive and negative electrodes, the liquid electrolyte solution of the invention is mixed with a suitable electrode-active material such as is known in the art, and any adjuvants thereto according to the practice in the art. In the case of the separator, if the separator is a porous body, the liquid electrolyte solution of the invention is imbibed within the pores. In the case of a semipermeable membrane, the liquid electrolyte solution of the invention is absorbed by the membrane. In the case of an ionomeric membrane, the liquid electrolyte solution of the invention is absorbed by the ionomer.

In another embodiment, the solid polymer electrolyte solution of the invention may itself be employed as the membrane separator in an electrochemical, preferably lithium battery, cell, or as the binder for the active particles in the anode and cathode.

In the practice of the invention, the electrolyte solution of the invention may be combined with one or more additional electrolytes such as are known in the art. Suitable electrolytes include low molecular weight lithium salts and ionic polymers, known as ionomers. Suitable low molecular weight lithium salts include both organic and inorganic salts such as $LiPF_6$, $LiBF_4$, $LiClO_4$, $LiAsF_6$, $LiN(SO_2CF_3)_2$, $LiN(SO_2CF_2CF_3)_2$, $LiC(SO_2CF_3)_3$, among others.

In a preferred embodiment, the electrode composition will additionally contain a polymeric binder and an electronically conductive additive such as carbon black such as Super P carbon black (MMM Carbon). In one preferred embodiment, wherein the separator is a copolymer of polyvinylidene fluoride and hexafluoropropylene (PVDF/HFP), such as that available under the trade name Kynar® obtainable from Atofina Chemicals, Philadelphia, Pa., the preferred binder is also PVDF/HFP. In an alternative preferred embodiment wherein the separator is an ionomer, the preferred binder will be the same or a closely related ionomer. Preferred ionomers are described in Doyle et al, U.S. Pat. No. 6,025,092 and Feiring et al, WO 99/50548.

By way of example, a suitable negative electrode for a lithium ion cell is formed by combining an aprotic solvent, preferably comprising a cyclic carbonate, most preferably ethylene or propylene carbonate, with a graphite-based electrode-active material, carbon black, and a polymeric binder in proportions of 62 parts graphite, 4 parts carbon black, 10 parts binder, and the remainder a liquid electrolyte solution of the invention to form an electrode composition. The electrode composition is then combined with the separator membrane, which may also be an embodiment of the electrolyte solution of the invention, and such other components as are deemed necessary or desirable, such as a current collector, a means for connecting the battery to a load, and so forth. In a preferred embodiment, the electrode composition is fed to a screw-type plasticating extruder wherein the combination is mixed, homogenized, and formed into a sheet or film by melt extrusion substantially according to the methods taught in Barton et al, WO 00/52085.

The other components of the lithium-ion cell of the invention may be formed in a similar fashion. The positive electrode of the lithium-ion cell of the present invention is preferably a mixture of a liquid electrolyte solution of the invention and a lithium-containing transition metal oxide which is capable of absorbing and releasing lithium-ions to a capacity of >100 mAh/g such as $LiCoO_2$, $LiNiO_2$, $LiNi_xCo_{1-x}O_2$, where 0.5<x<0.95, and $LiMn_2O_4$. The separator is formed by extrusion of a mixture of the electrolyte solution of the invention and the preferred ionomer, the mixture then extruded into a film or sheet.

The lithium-ion cell of the invention may be formed by any means such as is known in the art. The components of the cell may be first combined in the dry state, with the liquid electrolyte solution added as a late step in the process. Or, the liquid electrolyte solution may be added at any step in the process.

In the most preferred embodiment, the several layers of the different components of the lithium-ion cell of the invention are laminated together in a continuous process.

In another embodiment an electrode film is formed from 65 parts graphite mesocarbon microbeads such as MCMB, 3.25 parts carbon black, and 10 parts PVDF/HFP copolymer such as Kynar FLEX® 2801 as polymer binder, and the remainder dibutyl phthalate (Aldrich) as a plasticizer for the binder polymer. One method for forming the electrode film is to disperse or dissolve the components thereof in acetone, or other suitable solvents for PVDF/HFP, by heating up to ca. 60° C. to form a mixture followed by applying the mixture as a coating on a suitable substrate such as Mylar® polyester film (DuPont Company). Any means for coating the substrate may be employed such as solution casting using the well-known doctor-blade technique. The thus coated substrate is dried preferably at temperatures up to ca. 60° C. and then calendered or otherwise subject to contact pressure to compress the electrode coating to form a smooth surface. The dibutyl phthalate plasticizer is extracted by immersing the dried coated substrate into a volatile solvent such as diethyl ether or methanol for at least 15 minutes followed by drying under mild vacuum at room temperature for at least one hour. The film is separated from the substrate before or during the extraction step. The thus dried and extracted film can then be immersed into the liquid electrolyte solution of the invention.

EXAMPLES

Example 1

Grafting of PSEPVE onto Dodecane

A 500 mL 3-neck round bottom flask, equipped with a condenser, magnetic stirring, addition funnel, and gas inlet, was charged under a nitrogen atmosphere with 100 grams of anhydrous dodecane (Aldrich), 80 grams of PSEPVE made according to Connolly et al., U.S. Pat. No. 3,282,875, and 4 grams of t-butyl peroxide (Aldrich). The mixture was heated in an oil bath to 125° C. and stirred at this temperature for eight hours. The initially clear reaction mixture became cloudy as the reaction progressed. After eight hours, the mixture was allowed to cool to room temperature and was held overnight without stirring. Two clear layers were obtained. The top layer consisted mostly of unreacted dodecane and was decanted off. The bottom layer was transferred into a single-neck round bottom flask and was heated to 80° C. in a Kugelrohr apparatus at 0.5 mm Hg to evaporate any unreacted materials. 75 g of a clear viscous liquid were obtained.

$^1$H NMR (in CDCl$_3$) δ, ppm: 0.9–2.6 (m, hydrocarbon signals), 5.93 (d, CFH, J$_{FC-H}$=55 Hz). The ratio of these two signals was 7.1 indicating an average of 3.2 PSEPVE grafts per dodecane molecule.

$^{19}$F NMR δ, ppm: 45.0 (—SO$_2$F), −79 to −85 (two —CF$_2$O—, and —CF$_3$), −112.4. (—CF$_2$SO$_2$—), −117.3 (—CF$_2$-dodecane), −142.5 (—CFH—), −145.1 (—CF—).

Example 2

Grafting of PSEPVE onto n-Heptane

A stainless steel 600 mL high pressure reactor (Parr Instrument Co., Moline, Ill.) was charged with 100 mL of n-heptane (Aldrich), 10 grams of PSEPVE, and 1 gram of t-butyl peroxide (Aldrich). The reactor was closed and then it was purged and vented three times with nitrogen. Stirring was started and the reactor was heated to 80° C. After one hour the temperature was raised to 120° C., and after four more hours to 130° C. After one hour at 130° C. the temperature was raised again to 140° C. where it remained for the rest of the reaction time. Total reaction time was eight hours. After this time the reactor was cooled to room temperature where it remained overnight under nitrogen atmosphere. The reaction mixture was transferred to a 300 mL round bottom flask and the excess heptane was distilled off at atmospheric pressure. The remaining material was heated to 80° C. in a Kugelrohr apparatus at 0.5 mm Hg to evaporate any traces of unreacted materials. 10.2 g of a clear viscous liquid were obtained.

$^1$H NMR (in CDCl$_3$) δ, ppm: 0.9–2.6 (m, hydrocarbon signals), 5.95 (d, CFH, J$_{FC-H}$=55 Hz). The ratio of these two signals was 9.8 indicating an average of 1.5 PSEPVE grafts per heptane molecule.

$^{19}$F NMR (in CDCl$_3$) δ, ppm: 45.1 (—SO$_2$F), −79 to −86 (two —CF$_2$O—, and —CF$_3$), −112.4 (—CF$_2$SO$_2$—), −118 (—CF$_2$-heptane), −143.1 (—CFH—), −145.1 (—CF—).

Example 3

Preparation of PSEPVE-grafted Dodecane with Dicyanomethide Groups

A 500 mL 3-neck round bottom flask, equipped with a condenser, magnetic stirring, addition funnel, gas inlet, and under nitrogen atmosphere was charged with 25.7 grams of PSEPVE-grafted dodecane (containing an average of 2.8 PSEPVE grafts per molecule) prepared according to the method in Example 1, and 150 mL of anhydrous tetrahydrofuran (THF, Aldrich). After all the grafted dodecane dissolved, 1 gram of LiH (Aldrich) was added carefully in small portions. The reaction mixture was cooled to 0° C. and a solution of 4.15 grams of malononitrile (Aldrich) in 50 mL of THF was added dropwise over a period of two hours. After the addition the mixture was allowed to warm up to room temperature where it remained stirring overnight under nitrogen. Methanol (20 mL) was added to destroy any traces of unreacted LiH and then the solvent was removed in a rotary evaporator. The viscous yellowish liquid obtained was dissolved in 35 mL of distilled water and placed into a dialysis membrane (Spectra/Por® CE MWCO:500, Spectrum Laboratories, Inc. Calif.). It was dialyzed against deionized water for 48 hrs. After removing the water in a rotary evaporator and further drying in a vacuum oven, 9 grams of a yellowish amorphous solid were obtained.

Elemental analysis: % C=28.26, % H=1.52, % N=4.75, % F=42.30, % Li=1.62, % S=5.82. $^{19}$F NMR showed complete disappearance of the SO$_2$F resonance at 45 ppm. FTIR showed disappearance of the sulfonyl fluoride absorption near 1470 cm$^{-1}$ and the appearance of two bands at 2215 and 2237 cm$^{-1}$ attributed to the nitrile groups.

Solutions of this compound in propylene carbonate showed the following conductivities: 0.125 M: 1.03 mS/cm, 0.25 M: 1.41 mS/cm, 0.5 M: 1.37 mS/cm. A 1.0 M solution in a 2:1 solution of ethylene carbonate and dimethyl carbonate gave 1.3 mS/cm. Conductivity was determined using a VWR Scientific conductivity meter Model 2052.

Example 4

Preparation of PSEPVE-grafted Dodecane with Lithium Sulfonate Groups 4.238 g of LiOH.H$_2$O were dissolved in 50 mL H$_2$O and added to 50 mL acetone. 25 mL of this solution were added to 10.2879 g of the PSEPVE-grafted dodecane of Example 1. Two layers were formed and a white residue started to precipitate. 30 mL of water and 50 mL of acetonitrile were added and the reaction mixture was stirred for 24 h at room temperature.

$^{19}$F NMR of both layers after 24 h showed complete conversion of sulfonyl fluoride to sulfonate groups in the top layer and no conversion in the bottom layer. The layers were separated and the lower layer was dissolved in 25 mL of acetone. 25 mL of the LiOH solution were added to the acetone solution resulting in formation of a second layer. The mixture was heated to 50° C. After 16 h only one layer was present. $^{19}$F NMR analysis confirmed complete conversion of the sulfonyl fluoride to the sulfonate form. The reaction mixture was stirred at 55° C. over night. All volatiles were removed under vacuum and the residue was heated to 90° C. for 16 h. The residue was dissolved in 60 mL of deionized water and the solution placed into two dialysis tubes (Spectra/Por® CE, MWCO 100, Spectrum Laboratories, Inc. Calif.). The tubes were submerged into 4 l of deionized water. The water was changed until the pH did not rise above neutral and the pH of the solution inside the tube was around 7. The dialysis tubes were opened and the solutions were filtered to remove traces of solids. $^{19}$F NMR analysis of the solid residue in the tubes showed that this residue was mostly LiF. The water was removed from the solution by rotary evaporation. The residue was heated to 100° C. for 3.5 h. The product was slightly beige. Yield=10.1 g.

3.494 g of the material were dissolved in acetone. Charcoal was added and the mixture was filtered through Cellite® 545 after one hour stirring at room temperature. The color of the solution seemed unchanged. Charcoal was added again and the acetone solution was refluxed for two hours. The mixture was filtered and the acetone was removed. The nearly white residue was heated to 100° C. for 16 h under vacuum.

The remaining 6.5 g of the compound were treated with 50 mL of acetone. Insoluble LiF was filtered off. The solution was added to the previously dried material. The acetone was removed and the residue was dried for 16 h at 120° C.

Yield: 9.067 g $^{19}$F NMR (in CD$_3$CN) δ, ppm: −78 to −85 (m, CF$_3$ and CF$_2$O signals, 7F), −117.30 (s, CF$_2$SO$_2$, 2F), −115 to −125 (m, CF$_2$, 2F), −140 to −150 (m, CF, 2F). This confirmed complete conversion of sulfonyl fluoride groups to sulfonate.

$^1$H NMR (CD$_3$CN) δ, ppm: 6.24 (d, CFH, $^2$J(FH)=51.4 Hz), 3 to 0.5 (m, ethylene backbone). The ratio of the two signals confirmed that the number of grafts per dodecane molecule was the same as in the starting material.

A 0.5 M solution of this compound in EC/DEC (2:1 by weight) showed a conductivity of 0.74 mS/cm.

Example 5

Conversion of PSEPVE-grafted Dodecane into Imide Form with C$_3$SO$_2$NH$_2$ 20.003 g of PSEPVE-grafted dodecane of Example 1 was refluxed with 50 mL toluene overnight. 50 mL of the toluene were then distilled off to dry the compound. The flask was placed inside a dry-box and 6.050 g (40.6 mmol) CF$_3$SO$_2$NH$_2$ (TCI America, Portland Oreg.), and 75 mL of anhydrous triethylamine (Aldrich) was added. The reaction mixture was heated to a moderate reflux under argon atmosphere. The color of the mixture changed quickly from colorless over yellow to brown. A second, oily layer was formed at the bottom of the flask. After 24 hour under reflux, sulfonyl fluoride could not be detected by $^{19}$F NMR in the lower layer but was detected in the upper layer. The reaction mixture was refluxed for additional 24 h, 0.601 g (4.0 mmol) CF$_3$SO$_2$NH$_2$ were added and the mixture was refluxed for additional 24 h.

According to $^{19}$F NMR analysis, the conversion of sulfonyl fluoride was complete. All volatiles were removed under vacuum. The beige residue obtained was heated to 60° C. for 16 hours. The residue was washed eight times with 50 mL aliquots of water. The oily residue was heated to 45–55° C. with 50 mL water for 16 hours.

The oil layer was separated from the water and it was dried for 16 hours under vacuum at 60° C. The material was dissolved in acetonitrile and was treated with a 1 N aqueous LiOH solution for 2.5 hours at 60° C. The brown residue slowly dissolved in the LiOH solution and formed one phase. The solvent mixture was evaporated and the residue was dried under vacuum at 100° C. for 2 h. The material was dissolved in acetonitrile inside the dry-box and insoluble LiOH was filtered off. The acetonitrile was removed and the residue was dried at 100° C. for 24 h under vacuum. Yield: 12.560 g $^{19}$F NMR (in CD$_3$CN) δ, ppm: −78 to −86 (CF$_3$SO$_2$, CF$_3$CF, 2×CF$_2$O, 10 F); −117.6 (s, CF$_2$SO$_2$N, 2 F), −118.9 (s, CF$_2$SO$_3$, side product), −115 to −135 (CH$_2$CH—CF$_2$, 2 F) and −140 to −149 (CFH, CF(CF$_3$), 2F); This spectrum indicated that the product contained 21% of the ionic groups in the sulfonate form and 79% in the imide form.

$^1$H NMR (in CD$_3$CN) δ, ppm: 6.4 (CFH, 1H, $^2$J(FH) =54 Hz), 3 to 0.5 (m, ethylene backbone). The ratio of the two signals confirmed that the number of grafts per dodecane molecule was the same as in the starting material.

A 0.125 M of this compound in PC showed a conductivity of 1.1 mS/cm, while a 0.4 M solution in EC/DEC (2:1 by weight) had a conductivity of 2.2 mS/cm.

Example 6

Conversion of PSEPVE-grafted Dodecane into Imide Form with CF$_3$SO$_2$NNa$_2$

PSEPVE-grafted dodecane containing an average of 3.2 PSEPVE grafts per dodecane was refluxed with 100 mL toluene (EM Science) for 12 hours and then the toluene was distilled off to dry the compound.

Inside the dry-box a 250 mL round bottom flask was charged with 3.095 9 CF$_3$SO$_2$NH$_2$ and 100 mL anhydrous acetonitrile. 1.075 g NaH was added and the reaction was stirred for 6 hours at room temperature. 9.870 g of PSEPVE-grafted dodecane was added to the reaction mixture inside the dry-box. The reaction mixture was stirred at room temperature for 17 h. A trace of pure CF$_3$SO$_2$NNa$_2$ was added because an NMR indicated the conversion of the sulfonyl fluoride groups to be about 99%. The reaction mixture was stirred for 5 additional hours at room temperature. The light brown solution was centrifuged and the brown residue was washed with acetonitrile. The solvent from the combined liquid layers was evaporated under vacuum. The residue was heated for 16 hours to 100° C. at 10$^{-3}$ Torr. The yield was 12.178 g.

Inside the dry-box, this material was dissolved in 20 mL of anhydrous THF. 1.5 g of LiCl (Aldrich; dried for 5 hours at 130° C. and 10$^{-3}$ Torr) was dissolved in 70 mL of anhydrous THF. The two THF solutions were combined and stirred at room temperature for 1 hour. Upon combining the two solutions, the formation of NaCl could be observed. The reaction solution was filtered through a fine fritted glass filter. The solvent was removed under vacuum (10$^{-3}$ Torr) and the residue was heated for 16 h at 100° C. at 10$^{-3}$Torr.

The residue was dissolved in 50 mL of deionized water and the solution was placed into two dialysis tubes (Spectra/Por® CE, MWCO 500) to remove any low molecular weight salts remaining in the product. The tubes were submerged into 4 L of deionized water. The water was changed twice over the next 4 hours. After 6 h, the dialysis tubes were opened and the solutions were recovered. The water was removed under vacuum (10$^{-3}$ Torr) and the beige residue was heated to 100° C. at 10$^{-3}$ Torr for 16 hours. Yield was 8.5 g.

$^{19}$F NMR (in CD$_3$CN) δ, ppm: −74 to −88 (CF$_3$SO$_2$, CF$_3$CF, 2×CF$_2$O, 10 F); −110 to −137 (CH$_2$CH—CF$_2$, CF$_2$SO2, 4F) and −138 to −149 (CFH, CF(CF$_3$), 2F); this spectrum indicated complete conversion of the sulfonyl fluoride groups to the sulfonyl imide salt, and no hydrolysis to sulfonate was detectable.

$^1$H NMR (in CD$_3$CN) δ, ppm: 6.37 (CFH, 1 H, $^2$J(FH)=53 Hz), 3 to 0.5 (m, ehtylene backbone). The ratio of the two signals showed that the number of grafts per dodecane molecule was the same as in the starting material. Conversion to the desired product was complete.

Example 7

Grafting of Lithium N-trifluoromethyl perfluoro (3.6-dioxa-4-methyl-7-octenesulfonyl imide) (PSEPVE-imide) onto poly(ethylene glycol) dimethyl ether A 25 mL Schlenk tube equipped with magnetic stirrer was charged with 4 grams of PSEPVE-imide prepared according to Desmarteau, U.S. Pat. No. 5,463,005, and 6 grams of poly(ethylene glycol) dimethyl ether (Aldrich, Mw=250). The tube was evacuated and purged with nitrogen four times and then heated in an oil bath. The imide salt readily dissolved in the polymer when the temperature reached 60° C. When the temperature reached 125° C., 0.5 grams of t-butyl peroxide where added dropwise over a period of one hour. The mixture was stirred at 125° C. under nitrogen for a total of 6 hours. After cooling to room temperature the material was transferred to a vial and left under vacuum (0.5 mm Hg) overnight. 9.5 grams of a yellow viscous liquid were obtained.

1H NMR (in CDCl$_3$) d, ppm: 3.34 (s, CH$_3$O—), 3.4–3.7 (m, —CH$_2$CH$_2$O— chain), 6.2 (broad, CFH). The ratio of the signal at 3.4–3.7 to the 6.2 ppm signal indicated that there were on average 12 ethylene oxide repeats per PSEPVE-imide graft. The ratio of the 3.34 ppm signal to the 6.2 signal was 4 indicating that on average one half of the poly(ethylene glycol) dimethyl ether molecules had one PSEPVE-imide graft. 19F NMR (in CDCl$_3$) d, ppm: –77 to –88 (two —CF$_2$O—, —CF$_3$, and CF$_3$SO$_2$—), –116.5 (—CF$_2$SO$_2$—), –120 to –140 (—CF$_2$-polymer), –143 to –150 (—CFH—, and —CF—).

The ionic conductivity of this sample (neat) was 0.27 mS/cm. Conductivity was determined according to the protocol of Doyle et al., WO 9820573(A1) but where the sample holder was modified to provide a depression for holding a fluid. The apparatus was designed so that the conductivity determined was a surface conductivity using the four point probe method of Doyle et al, op. cit.

Example 8

A lithium-ion type 2032 coin cell was prepared using procedures known in the art. The coin cell parts (can, lid, spacer, and gasket) and coin cell crimper were purchased from Hohsen Corp. The positive electrode used in the coin cell was solution cast from acetone, dried in air, and 12 mm circular sections were punched out using brass punches. The positive electrode film had a composition of 65 parts LiCoO$_2$ (FMC Corp.), parts Kynar FLEX® 2801 (Elf Atochem), and 6.5 parts Super P carbon black (MMM Carbon). The remainder of the electrode contained dibutyl phthalate (Aldrich) as plasticizer which was removed by extraction with diethyl ether for 30 minutes followed by drying under vacuum at 23° C. for one hour. The anode consisted of four 12 mm diameter disks of lithium foil 3 mil thick. Both anode and cathode films were sandwiched around a 18 mm diameter sheet of 26 micron thick Celgard® 3501 (Celanese Corp.) separator film.

The electrolyte solution was obtained by dissolving 5.5493 grams of PSEPVE-grafted dodecane with dicyanomethide groups described in example 3 into a solution composed of 2 parts by weight of EC (Selectipur®, 99+%, EM Industries) and 1 part by weight of DMC (Selectipur®, 99+%, EM Industries) to make 10 mLs of solution. The cathode and separator films were soaked in electrolyte solution for one hour prior to assembly of the coin cell inside an argon-purged Vacuum Atmospheres glove box.

The coin cell was first charged using 0.5 mA current to an upper cutoff voltage of 4.2 V. The cell was then discharged at 0.5 mA to a discharge cutoff potential of 3.0 V. The cell was cycled between these voltages and the capacity at each cycle was measured. The difference between the capacity on the very first charge and the capacity on the subsequent first discharge, represented as a ratio of capacities (discharge capacity/charge capacity), is referred to as the reversible capacity. The capacity of the coin cell on the first charge was 1.87 mAh while the capacity returned on the first discharge was 1.76 mAh giving a reversible capacity of 94%.

The cycle life of the coin cell is defined as the first cycle that achieves only 80% of the initial capacity of the cell. The cycle life for this cell was 165 cycles.

Example 9

Solid Polymer Electrolyte Using PEO-g-PSEPVE-imide with Poly(ethylene glycol) Methyl Ether Acrylate Poly(ethylene glycol) methyl ether acrylate, 450 molecular weight (H$_2$C=CHCO$_2$(CH$_2$CH$_2$O)$_n$CH$_3$, CAS 32171-39-4, Aldrich product #45,499-0) was passed through a column of alumina (ICN Alumina N,Akt.I, from Bodman Industries, Aston, Pa.) to remove the inhibitor. The liquid was then taken to a nitrogen dilled dry box and molecular sieves added to dry the liquid for over 4 days.

A graft oligomer of PSPEVE-imide and polyethylene oxide (250 Daltons) was synthesized according to the method of Example 7 except that 4 grams of PSEPVE-imide, 4 grams of polyethylene glycol dimethyl ether, and 0.3 grams of t-butyl oxide were employed. The mole ratio of Li to ethylene oxide linkage was 1:13.

In a nitrogen filled dry box, 2.0137 g of PSEPVE-imide-grafted polyethylene oxide so-formed, 1.4340 g of the treated poly(ethylene glycol) methyl ether acrylate and 0.0220 g of diphenyl(2,4,6-trimethylbenzoyl)phosphine oxide initiator was mixed in a glass vial and cast into a film using a doctor blade. The film was allowed to cure under ambient laboratory light for about 30 min. and then placed under a VWR Scientific Model UVGL25 4.5W UV-254 nm lamp for 3 days. A rubbery film was formed.

The mole ratio of Li to ethylene oxide linkage was calculated to be 1:29.

The conductivity of the film was determined to be 0.061 mS/cm per the 4 conductor probe method of Doyle et al., WO 9820573(A1).

What is claimed is:

1. A composition comprising a saturated acyclic aliphatic hydrocarbon radical, said hydrocarbon radical having disposed thereupon at least one pendant group represented by the formula

wherein said hydrocarbon radical is optionally substituted with one or more ether oxygens;

wherein R$_f$ is represented by the formula

where a=0 or 1, b=0 or 1, c=0,1 or 2; —Q— is represented by the formula

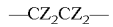

where Z is H, F, alkyl or fluoroalkyl with the proviso that not more than one Z may be alkyl or fluoroalkyl: R$_f$' is F or a perfluoroalkyl radical having 1–10 carbons optionally substituted by one or more ether oxygens; X is F or —Y(M)(SO$_2$R$_f$'')$_p$ wherein p=0–2, with the proviso that Y is O when p=0, Y is N when p=1, and Y is C when p=2, M is an alkali metal cation or H$^+$, and R$_f$'' is a perfluoroalkyl radical having 1–10 carbons optionally substituted with one or more ether oxygens, or R$_f$'' is CN when p=2.

2. The composition of claim 1 wherein the hydrocarbon radical is a radical having 6–30 carbons chain optionally substituted by one or more ether oxygens, or is a radical formed from a poly(ethylene oxide) of molecular weight between 100 and 2000 daltons.

3. The composition of claim 2 wherein said hydrocarbon radical is derived from dodecane.

4. The composition of claim 2 wherein said hydrocarbon radical is derived from poly(ethylene oxide) having a molecular weight between 100 and 2000 Daltons.

5. The composition of claim 1 wherein, in said pendant group, Z is F or H, a=0 or 1, b=1, c=0 or 1, and X is F, with the proviso that when Z is H, a=0.

6. The composition of claim 1 wherein, in said pendant group, Z is F, a=1, b=1, and c=1, and X is F.

7. A process for forming a composition, the process comprising contacting in the presence of a free radical initiator a saturated acyclic aliphatic hydrocarbon optionally substituted with one or more ether oxygens, with an olefinically unsaturated fluorocarbon and, heating in order to decompose the initiator and form free radicals; said olefinically unsaturated fluorocarbon being represented by the formula $$CZ_2=CZ-O_a-(CF_2CFR_f'-O_b)_cCF_2CF_2-SO_2X$$

where Z is H, F, alkyl or fluoroalkyl with the proviso that not more than one Z may be alkyl or fluoroalkyl; Rf' is F or a perfluoroalkyl radical having 1–10 carbons optionally substituted by one or more ether oxygens; and X is F or —Y(M)(SO2Rf'')$_p$ wherein p=0–2, with the proviso that Y is O when p=0, Y is N when p=1, and Y is C when p=2, M is an alkali metal cation or H+, and Rf'' is a perfluoroalkyl radical having 1–10 carbons optionally substituted with one or more ether oxygens.

8. The process of claim 7 wherein said olefinically unsaturated fluorocarbon is in the form of a sulfonate, imide, of methide, and said saturated aliphatic hydrocarbon optionally substituted by one or more ether oxygens is an aliphatic polyether.

9. The process of claim 8 wherein said polyether is poly(ethylene oxide) of molecular weight between 100 and 2000 daltons.

10. The process of claim 7 wherein the saturated aliphatic hydrocarbon optionally substituted by one or more either oxygens is dodecane.

11. An electrolyte composition comprising a liquid, a polymer, or a mixture thereof combined with a composition comprising a saturated acyclic aliphatic hydrocarbon radical optionally substituted with one or more ether oxygens, said hydrocarbon radical having disposed thereupon at least one pendant group represented by the formula

wherein $R_f$ is represented by the formula $$-Q-O_a-(CF_2CFR_f'-O_b)_cCF_2CF_2-$$

where a=0 or 1, b=0 or 1, c=0,1 or 2; —Q— is represented by the formula $$-CZ_2CZ_2-$$

where Z is H, F, alkyl or fluoroalkyl with the proviso that not more than one Z may be alkyl or fluoroalkyl; $R_f'$ is F or a perfluoroalkyl radical having 1–10 carbons optionally substituted by one or more ether oxygens; X is F or —Y(M)(SO$_2R_f''$)$_p$ wherein p=0–2, with the proviso that Y is O when p=0, Y is N when p=1, and Y is C when p=2, M is an alkali metal cation or H$^+$, and $R_f''$ is a perfluoroalkyl radical having 1–10 carbons optionally substituted with one or more ether oxygens, or $R_f''$ is CN when p=2.

12. The electrolyte composition of claim 11 wherein the liquid is selected from the group consisting of dimethyl carbonate (DMC), diethyl carbonate (DEC), ethyl methyl carbonate (EMC), propylene carbonate (PC), and ethylene carbonate (EC), most preferably EC or PC, and monoesters such as methyl acetate (MA), ethyl acetate (EA), methyl formate (MF), methyl propionate (MP), ethyl propionate (EP), gamma-butyrolactone (GBL), dimethyl succinate and mixtures thereof.

13. The electrolyte composition of claim 11 wherein the liquid is a mixture of a cyclic carbonate and an acyclic carbonate.

14. The electrolyte composition of claim 12 wherein the cyclic carbonate is ethylene carbonate, propylene carbonate, or a mixture thereof, and the acyclic carbonate is dimethyl carbonate, diethylcarbonate, ethyl-methyl carbonate, or a mixture thereof.

15. The electrolyte composition of claim 11 comprising a polymer wherein the polymer is a polyether, polyetheracrylate, polyethermethacrylate, comb-shaped polyethers, polyvinyl ether, or poly[bis-(methoxyexothyethoxide)phosphazene] and mixtures thereof.

16. The electrolyte composition of claim 15 wherein the polymer is polyethylene oxide or poly(polyethylene glycol) methyl ether acrylate.

17. The electrolyte composition of claim 11 wherein the hydrocarbon radical is a radical having 6–30 carbons optionally substituted by one or more ether oxygens, or is a radical formed from a polyether of molecular weight between 100 and 2000 daltons.

18. The electrolyte composition of claim 17 wherein the hydrocarbon radical is derived from dodecane.

19. The electrolyte composition of claim 17 wherein said hydrocarbon radical is derived from poly(ethylene oxide) having a molecular weight between 100 and 2000 Daltons.

20. An electrochemical cell comprising a positive electrode, a negative electrode, a separator, and an electrolyte solution, in ionically conductive contact with one another, said electrolyte solution comprising a liquid or a polymer combined with a composition comprising a saturated acyclic aliphatic hydrocarbon radical optionally substituted with one or more ether oxygens, said hydrocarbon radical optionally substituted with one or more ether oxygens having disposed thereupon at least one pendant group represented by the formula

wherein $R_f$ is represented by the formula $$-Q-O_a-(CF_2CFR_f'-O_b)_cCF_2CF_2-$$

where a=0 or 1, b=0 or 1, c=0,1 or 2; —Q— is represented by the formula $$-CZ_2CZ_2-$$

where Z is H, F, alkyl or fluoroalkyl with the proviso that not more than one Z may be alkyl or fluoroalkyl; $R_f'$ is F or a perfluoroalkyl radical having 1–10 carbons optionally substituted by one or more ether oxygens; X is F or —Y(M)(SO$_2R_f''$)$_p$ wherein p=0–2, with the proviso that Y is O when p=0, Y is N when p=1, and Y is C when p=2, M is an alkali metal cation or H$^+$, and $R_f''$ is a perfluoroalkyl radical having 1–10 carbons optionally substituted with one or more ether oxygens, or $R_f''$ is CN when p=2.

21. The electrochemical cell of claim 20 in the form of a lithium or lithium-ion cell.

22. The electrochemical cell of claim 20 wherein the separator is an ionomer.

23. The electrochemical cell of claim 20 wherein the separator is a copolymer of polyvinylidene fluoride and hexafluoropropylene.

24. The electrochemical cell of claim 20 wherein the separator comprises an aliphatic polyether or a polyether acrylate.

25. The electrochemical cell of claim 20 or claim 21 wherein the hydrocarbon radical is formed from a radical having 6–30 carbons disposed in a linear chain optionally substituted by one or more ether oxygens, or is a radical formed from an aliphatic polyether of molecular weight between 100 and 2000 daltons.

26. The electrochemical cell of claim 20 or 21 wherein said hydrocarbon radical is derived from dodecane.

27. The electrochemical cell of claim 20 or 21 wherein said hydrocarbon radical is derived from poly(ethylene oxide) having a molecular weight between 100 and 2000 Daltons.

28. The electrochemical cell of claim 20 wherein in the electrolyte solution, the polymer is an aliphatic polyether or a polyether acrylate.

29. The electrochemical cell of claim 28 wherein the polymer is polyethylene oxide or poly(polyethylene glycol) methyl ether acrylate.

* * * * *